United States Patent
Orbay (10) Patent No.: US 7,250,053 B2
(45) Date of Patent: Jul. 31, 2007

(54) LOW PROFILE DISTAL RADIUS FRACTURE FIXATION PLATE

(75) Inventor: Jorge L. Orbay, Miami, FL (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/985,596

(22) Filed: Nov. 10, 2004

(65) Prior Publication Data

US 2005/0065522 A1 Mar. 24, 2005

Related U.S. Application Data

(63) Continuation-in-part of application No. 10/689,797, filed on Oct. 21, 2003, which is a continuation-in-part of application No. 10/664,371, filed on Sep. 17, 2003, which is a continuation-in-part of application No. 10/401,089, filed on Mar. 27, 2003, now Pat. No. 6,866,665.

(51) Int. Cl.
*A61B 17/56* (2006.01)
(52) U.S. Cl. .................................. 606/69
(58) Field of Classification Search ............ 606/69–71
See application file for complete search history.

(56) References Cited

U.S. PATENT DOCUMENTS

| | | | |
|---|---|---|---|
| 3,741,205 A | | 6/1973 | Markolf et al. |
| 4,506,662 A | | 3/1985 | Anapliotis |
| 4,565,193 A | * | 1/1986 | Streli .................. 606/69 |
| 4,794,919 A | | 1/1989 | Nisson |
| 4,867,144 A | | 9/1989 | Karas et al. |
| 5,006,120 A | * | 4/1991 | Carter .................. 606/69 |
| 5,015,248 A | | 5/1991 | Burstein et al. |
| 5,151,103 A | | 9/1992 | Tepic et al. |
| 5,197,966 A | * | 3/1993 | Sommerkamp .......... 606/69 |
| 5,304,180 A | | 4/1994 | Slocum |
| 5,527,311 A | | 6/1996 | Procter et al. |
| 5,586,985 A | * | 12/1996 | Putnam et al. .......... 606/69 |
| 5,601,553 A | | 2/1997 | Trebing et al. |
| 5,676,667 A | | 10/1997 | Hausman |
| 5,709,682 A | | 1/1998 | Medoff |

(Continued)

OTHER PUBLICATIONS

"SCS™/D Distal Radius Plate System: Dorsal", Avanta, 1997.

(Continued)

*Primary Examiner*—Eduardo C. Robert
*Assistant Examiner*—Mary Hoffman
(74) *Attorney, Agent, or Firm*—Gordon & Jacobson, PC (57) ABSTRACT

A fixation plate includes a set of threaded peg holes adapted to individually receive fixation pegs therethrough and non-threaded alignment holes having a relatively smaller diameter than the peg holes and preferably sized to closely receive a K-wire. The alignment holes are located between the peg holes. One alignment hole is configured for aligning the plate during an osteotomy procedure, while other alignment holes are configured for use after fracture reduction and receive K-wires to temporarily stabilize the fracture and secure the plate to the bone and determine whether pegs inserted through adjacent respective peg holes will be properly located before drilling relatively larger holes for such pegs. The head of the plate has a shape and contour which provides bone support and a low profile which minimizes the potential for soft tissue irritation.

21 Claims, 8 Drawing Sheets

U.S. PATENT DOCUMENTS

| | | | |
|---|---|---|---|
| 5,709,686 A * | 1/1998 | Talos et al. | 606/69 |
| 5,718,705 A | 2/1998 | Sammarco | |
| 5,749,872 A * | 5/1998 | Kyle et al. | 606/69 |
| 5,772,662 A | 6/1998 | Chapman et al. | |
| 5,853,413 A * | 12/1998 | Carter et al. | 606/69 |
| 5,931,839 A | 8/1999 | Medoff | |
| 5,938,664 A | 8/1999 | Winquist et al. | |
| 5,941,878 A | 8/1999 | Medoff | |
| 5,968,047 A * | 10/1999 | Reed | 606/76 |
| 6,096,040 A * | 8/2000 | Esser | 606/69 |
| 6,221,073 B1 * | 4/2001 | Weiss et al. | 606/60 |
| D443,060 S * | 5/2001 | Benirschke et al. | D24/155 |
| 6,270,499 B1 | 8/2001 | Leu et al. | |
| 6,283,969 B1 * | 9/2001 | Grusin et al. | 606/69 |
| 6,355,041 B1 | 3/2002 | Martin | |
| 6,358,250 B1 * | 3/2002 | Orbay | 606/69 |
| 6,364,882 B1 | 4/2002 | Orbay | |
| 6,379,359 B1 | 4/2002 | Dahners | |
| 6,440,135 B2 | 8/2002 | Orbay et al. | |
| 6,468,278 B1 | 10/2002 | Muckter | |
| 6,527,775 B1 * | 3/2003 | Warburton | 606/62 |
| 6,623,486 B1 * | 9/2003 | Weaver et al. | 606/69 |
| 7,090,676 B2 * | 8/2006 | Huebner et al. | 606/71 |
| 2001/0011172 A1 * | 8/2001 | Orbay et al. | 606/69 |
| 2002/0032446 A1 * | 3/2002 | Orbay | 606/69 |
| 2002/0156474 A1 * | 10/2002 | Wack et al. | 606/69 |
| 2003/0073999 A1 | 4/2003 | Putnam | |
| 2003/0105461 A1 | 6/2003 | Putnam | |
| 2003/0153918 A1 * | 8/2003 | Putnam et al. | 606/69 |
| 2004/0059334 A1 | 3/2004 | Weaver et al. | |
| 2004/0059335 A1 | 3/2004 | Weaver et al. | |
| 2005/0010226 A1 * | 1/2005 | Grady et al. | 606/69 |
| 2005/0085818 A1 * | 4/2005 | Huebner | 606/69 |

OTHER PUBLICATIONS

"SCS™/V Distal Radius Plate: Volar", Avanta, 1998.

"The Distal Radius Plate Instrument and Implant Set", Technique Guide, SYNTHES®, Paoli, PA, 1995.

"Advances in distal Radius Fracture Management(D)", transcript of American Academy of Orthopaedic Surgeons 2001 Conference, pp. 134-151, Feb. 28, 2001, Including article by Matthew D. Putnam, MD, entitled "Repair and Rehabilitation of Distal Radius Fractures:: The Role of Subchondral Fixation" at pp. 144-147.

Summary of Safety and Effectiveness Information for Synthes Condylar Buttress Plates; Synthes USA.

Biomechanics in Uniaxial Compression of Three Distal Radius Volar Plates D. Osada; S. Fujita, K. Tamai, A. Iwamoto, K. Tomizawa, K. Saotome; the Journal of Hand Surgery; 2004.

Surgical Innovations; Advances in Distal Radius Fixation; J. Orbay MD; Mar./Apr. 2003.

* cited by examiner

LOW PROFILE DISTAL RADIUS FRACTURE FIXATION PLATE

This application is a continuation-in-part of U.S. Ser. No. 10/689,797, filed Oct. 21, 2003, which is a continuation-in-part of U.S. Ser. No. 10/664,371, filed Sep. 17, 2003, which is a continuation-in-part of U.S. Ser. No. 10/401,089, filed Mar. 27, 2003 now U.S. Pat. No. 6,866,655, both of which are hereby incorporated by reference herein in their entireties.

BACKGROUND OF THE INVENTION

1. Field of the Invention

This invention relates broadly to surgical implants. More particularly, this invention relates to a bone fracture fixation system for distal radius fractures.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture (occurring at the extremity of a shaft of a long bone) are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic. Plating utilizes a stabilizing metal plate typically placed against the dorsal side of a bone, and screws extending from the plate into holes drilled in the bone fragments to provide stabilized fixation of the fragments. However, many currently available plate systems fail to provide desirable alignment and stabilization.

In particular, with a distal radius fracture the complex shape of the distal radius, including the prominent volar rim of the lunate fossa, relatively flat volar rim of the scaphoid fossa, and the sometimes prominent base of the styloid process should be accommodated. Furthermore, the ligaments extending from the volar side of the distal radius to the intercarpal bones must not be irritated or distressed. Moreover, a fixation device should provide desirable alignment and stabilization of the bone structure proximate the articular surface of the distal radius.

SUMMARY OF THE INVENTION

It is therefore an object of the invention to provide an improved fixation system for distal radius fractures.

It is another object of the invention to provide a distal radius volar fixation system that desirably aligns and stabilizes multiple bone fragments in a fracture to permit proper healing.

It is also an object of the invention to provide a distal radius volar plate system which provides support for articular and subchondral surfaces.

It is an additional object of the invention to provide a distal radius volar plate system which accommodates the anatomical structure of the metaphysis of the distal radius.

It is a further object of the invention to provide a distal radius volar plate system which provides support without interfering with ligaments and soft tissues near the edge of the articular surface.

In accord with these and other objects, which will be discussed in detail below, a distal radius volar fixation system is provided. The system generally includes a plate intended to be positioned against the volar side of the radius, a plurality of bone screws for securing the plate to the proximal fragment of the radius bone, a plurality of bone pegs sized to extend from the plate and into bone fragments at the metaphysis of a radius bone, and one or more K-wires to facilitate alignment and fixation of the plate over the bone and guide the process of application. Preferred bone pegs and peg holes within the plate are provided which facilitate entry and retention of the bone pegs within the peg holes.

The plate is generally T-shaped, defining an elongate body and a generally transverse head angled upward relative to the body, and includes a first side which is intended to contact the bone, and a second side opposite the first side. The body includes a plurality of countersunk screw holes for the extension of the bone screws therethrough, and optionally one or more substantially smaller K-wire alignment holes. The lower surfaces of the radial and ulnar side portions of the head are contoured upward (in a Z direction) relative to the remainder of the head to accommodate the prominent volar rim of the lunate fossa, the relative flat volar rim of the scaphoid fossa and the prominent ridge at the base of the styloid process. An extension is provided at the head portion along the distal ulnar side of the head to buttress the volar lip (marginal fragment) of the lunate fossa of the radius bone, thereby providing support to maintain the wrist within the articular socket in case of fracture of this very essential area. Moreover, the contoured shape provides a stable shape that prevents rocking of the plate on the bone and maintains anatomical alignment between the fracture fragments. The upper and lower surfaces are chamfered to have a reduced profile that limits potential interface with ligaments and soft tissues near the edge of the lunate fossa. The head includes a plurality of threaded peg holes for receiving the pegs therethrough. The peg holes are arranged into a first set provided in a proximal portion of the head, and a second relatively distal set preferably provided in the tapered portion of the head.

The first set of the peg holes is substantially linearly arranged generally laterally across the head. The line of pegs is preferably slightly oblique relative to a longitudinal axis through the body of the plate. Axes through the first set of holes are preferably oblique relative to each other, and are preferably angled relative to each other in two dimensions such that pegs inserted therethrough are similarly obliquely angled relative to each other. The pegs in the first set of peg holes provide support for the dorsal aspect of the subchondral bone fragments.

The second set of peg holes is provided relatively distal of the first set. The holes of the second set, if more than one are provided, are slightly out of alignment but generally linearly arranged. The pegs in the second set of peg holes provide support for the volar and central aspects of the subchondral bone, behind and substantially parallel to the articular bone surface.

A distal alignment hole is provided generally between two peg holes of the second set of peg holes. At the upper surface of the plate, the distal alignment hole is substantially circular, while at the lower surface, the hole is laterally oblong. One or more proximal alignment holes of a size substantially smaller than the peg holes are provided substantially along a distal edge defined by a tangent line to shafts of pegs inserted in the first set of peg holes, and facilitates temporary fixation of the fracture fragments and of the plate to the bone with K-wires. Furthermore, along the body two longitudinally displaced alignment holes are also provided. All of the alignment holes are sized to closely receive individual K-wires.

The plate may be used in at least two different manners. According to a first use, the surgeon reduces a fracture and aligns the plate thereover. The surgeon then fixes the elongated body portion of the plate to the proximal radius fragment and then drills K-wires through the proximal row of alignment holes on the head portion of the plate to temporarily fix the orientation of the head of the plate to the distal fragment. Once the alignment is so fixed, the fracture is examined, e.g., under fluoroscopy, to determine whether the fracture is reduced in an anatomically correct manner and if the K-wires are properly aligned relative to the articular surface. As the axes of the proximal alignment holes closely correspond to axes of adjacent peg holes and the distal edges of the K-wires closely corresponds to the distal edges of the adjacent pegs, the fluoroscopically viewed K-wires provide an indication as to whether the pegs will be properly oriented in relation to the subchondral bone of the distal fragment. If the placement is correct, the K-wires maintain the position of the plate over the fracture. The peg holes may then be drilled with confidence that their locations and orientations are proper. If placement is not optimal, the K-wires can be removed and the surgeon has an opportunity to relocate and/or reorient the K-wires and drill again. Since each K-wire is of relatively small diameter, the bone is not significantly damaged by the drilling process and the surgeon is not committed to the initial drill location and/or orientation.

According to a second use, the plate may be used to correct a metaphyseal deformity (such as a malunited fracture or congenital deformity). For such purposes, a K-wire is drilled, e.g., under fluoroscopy, into the bone immediately underneath and parallel to the articular surface in the lateral view until one end of the K-wire is located within or through the bone and the other end is free. The free end of the K-wire is guided through the distal oblong alignment hole of the head of the plate, and the plate is slid down over the K-wire into position against the bone. The oblong alignment hole permits the plate to tilt laterally over the K-wire to sit flat on the bone, but does not permit movement of the plate over the K-wire in the anterior-posterior plane. The surgeon drills holes in the bone in alignment with the peg holes and then fixes the plate relative the bone with pegs. The bone is then cut, and the body of the plate is levered toward the shaft of the bone to re-orient the bone. The body of the plate is then fixed to the shaft to correct the anatomical defect.

Additional objects and advantages of the invention will become apparent to those skilled in the art upon reference to the detailed description taken in conjunction with the provided figures.

DETAILED DESCRIPTION OF THE PREFERRED EMBODIMENTS

Turning now to FIGS. 1 through 6, a fracture fixation system 100 according to the invention is shown. The system 100 is particularly adapted for aligning and stabilizing multiple bone fragments in a dorsally displaced distal radius fracture (or Colles' fracture). The system 100 generally includes a substantially rigid T-shaped plate 102, commonly called a volar plate, bone screws 104 (FIG. 3), pegs 106, 108, and K-wires 110 FIGS. 5 and 6). Pegs 106 have a threaded head and a non-threaded shaft, and pegs 108 have both a threaded head and a threaded shaft. Either pegs 106 or 108, or a combination thereof may be used at the discretion of the surgeon. Exemplar pegs are described in more detail in U.S. Pat. No. 6,364,882, which is hereby incorporated by reference herein in its entirety.

Figures 5, 6:
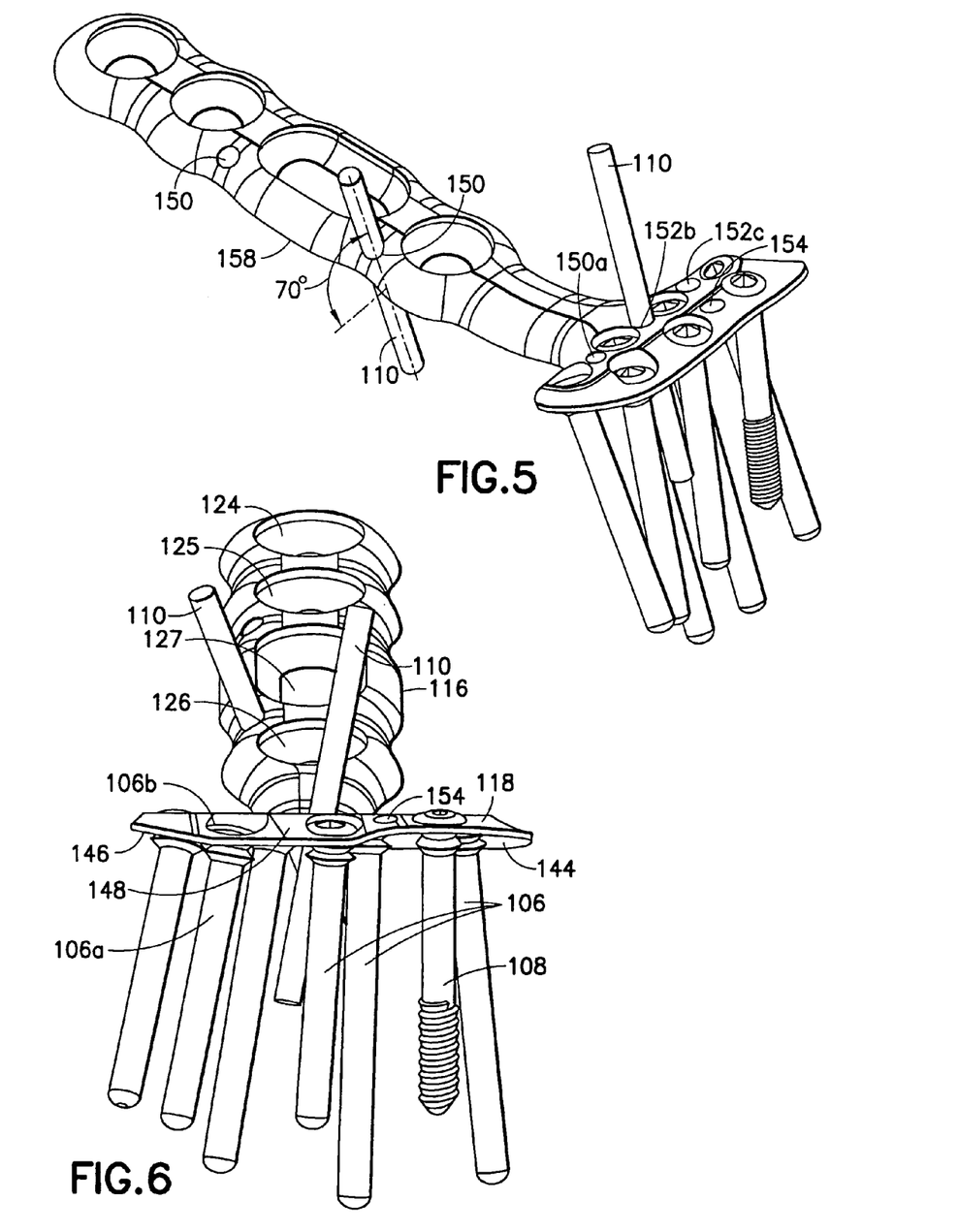
FIG. 5 is a perspective view of a right-hand volar plate according to the invention, shown with pegs coupled thereto and K-wires extending through body portion alignment holes and through proximal head alignment holes.
FIG. 6 is a front end view of a right-hand volar plate according to the invention, shown with pegs coupled thereto and K-wires extending through body portion alignment holes and proximal head alignment holes.
Figure 13:
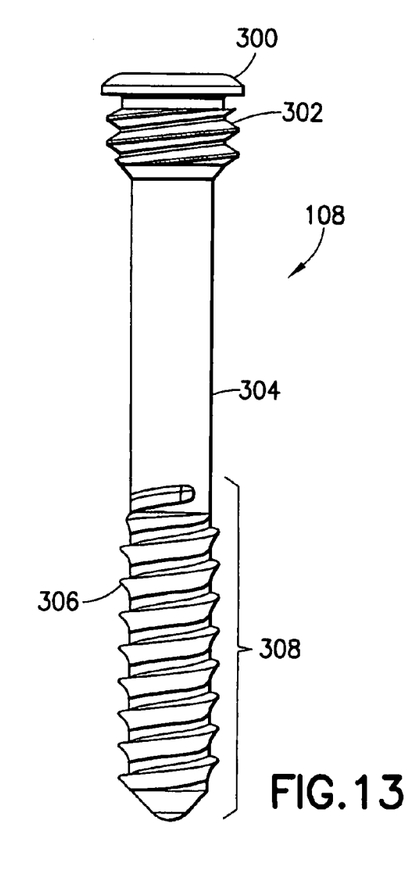
FIG. 13 is a side elevation of a partially threaded peg according to the invention.

In addition, a preferred partially threaded shaft peg 108 is shown best in FIGS. 6 and 13. Peg 108 includes a head portion 200 with preferably a single helical machine thread 202 of a first pitch and a shaft 204 portion having one or more threads 206 of a larger second pitch. (The head portion of non-threaded shaft pegs 106 also preferably includes a single helical thread.) The threads 206 preferably extend along a distal portion 208 of the shaft 204, and most preferably where such distal portion comprises approximately one-half the length of the shaft. Alternatively, or in addition, one or more pegs may be used where the threads extend along substantially the entirety, or the entirety, or the length of the shaft.

Figure 15:
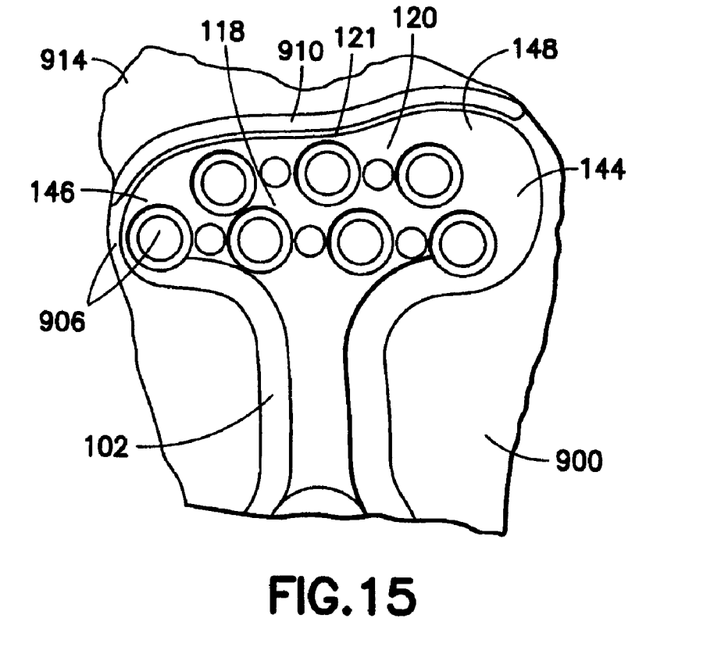
FIG. 15 is a broken volar view of the distal portion of a left-hand volar plate coupled on a volar side of a distal radius bone according to the invention.
Figure 16:
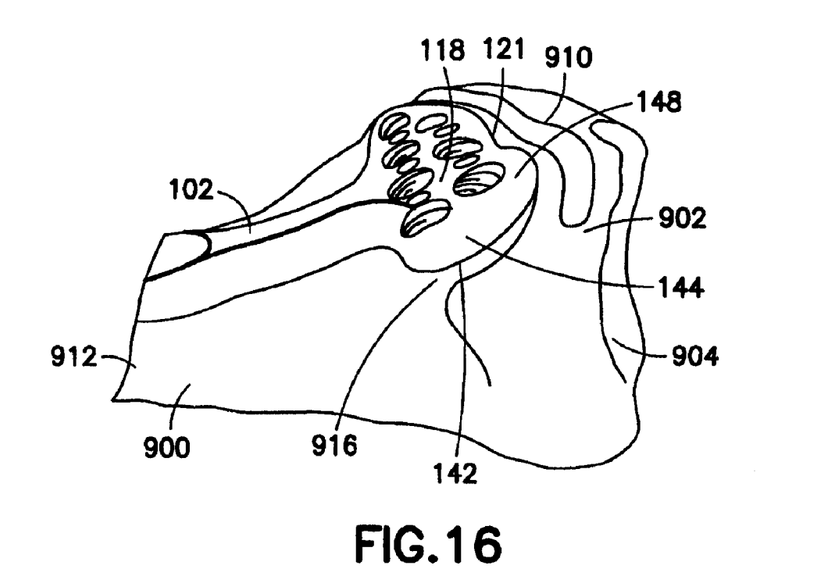
FIG. 16 is a broken ulnar side view of the distal portion of a left hand volar plate coupled on a volar side of a distal radius bone according to the invention.

The volar plate 102 shown in FIGS. 1-6 is a right-hand plate intended to be positioned against the volar side of a fractured radius bone of the right arm. It is appreciated that a left-hand volar plate (as shown in FIGS. 15 and 16) is substantially a mirror image of the plate shown and now described. The T-shaped plate 102 defines an elongate body 116, and a head 118 angled upward (in the Z-direction) relative to the body. The angle α in the Z-direction between the head 118 and the body 116 is preferably approximately 25°. The head 118 includes a distal buttress 120 (i.e., the portion of the head distal a first set of peg holes 134, discussed below), which tapers in thickness toward a distal edge 121. The thickest portion of the plate 102 has a thickness of preferably approximately 0.1 inch (2.5 mm), and is preferably made from a titanium alloy, such as Ti-6Al-4V.

Figures 1, 2:
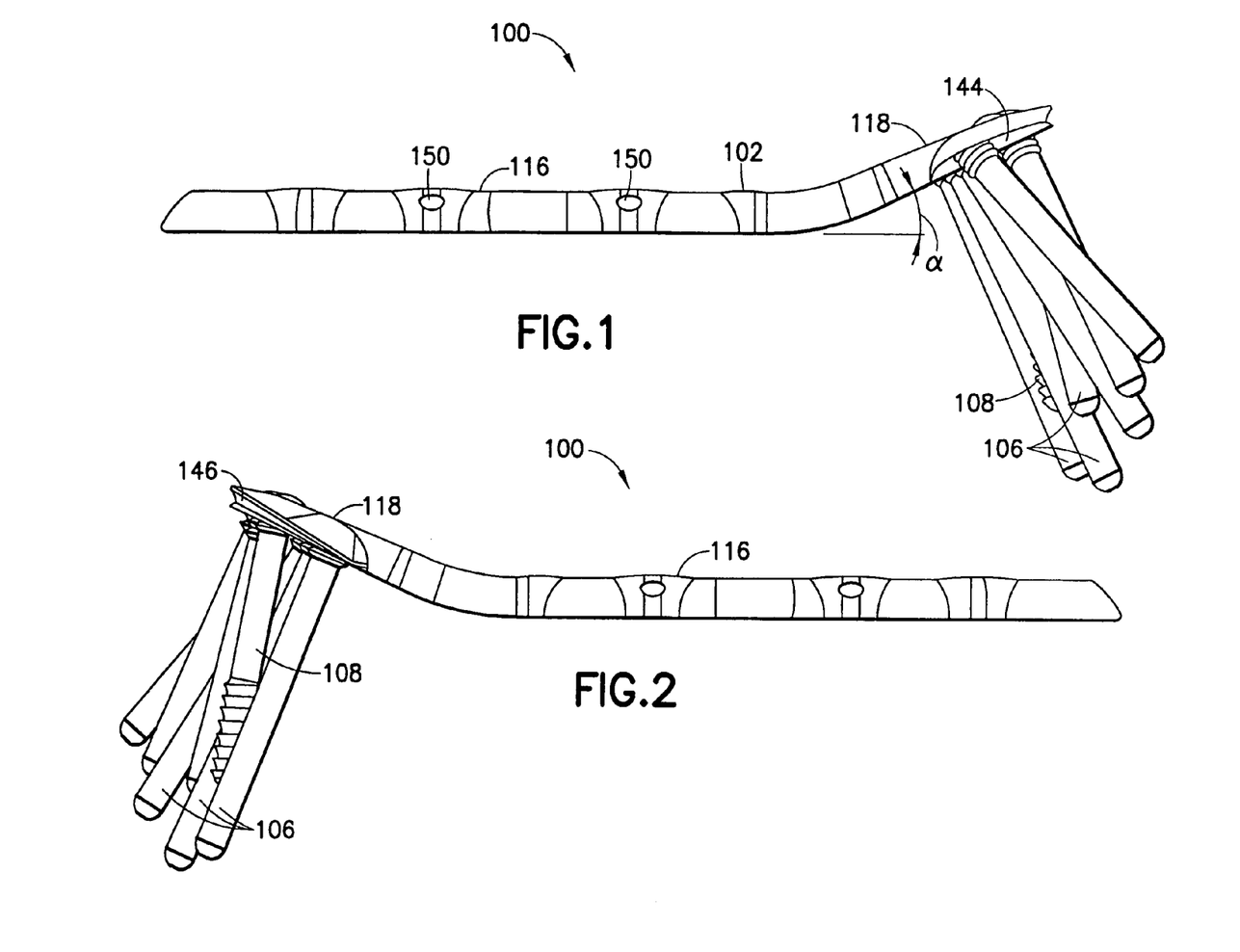
FIG. 1 is a radial side elevation of a right-hand volar plate according to the invention, shown with pegs coupled thereto.
FIG. 2 is an ulnar side elevation of a right-hand volar plate according to the invention, shown with pegs coupled thereto.
Figure 4:
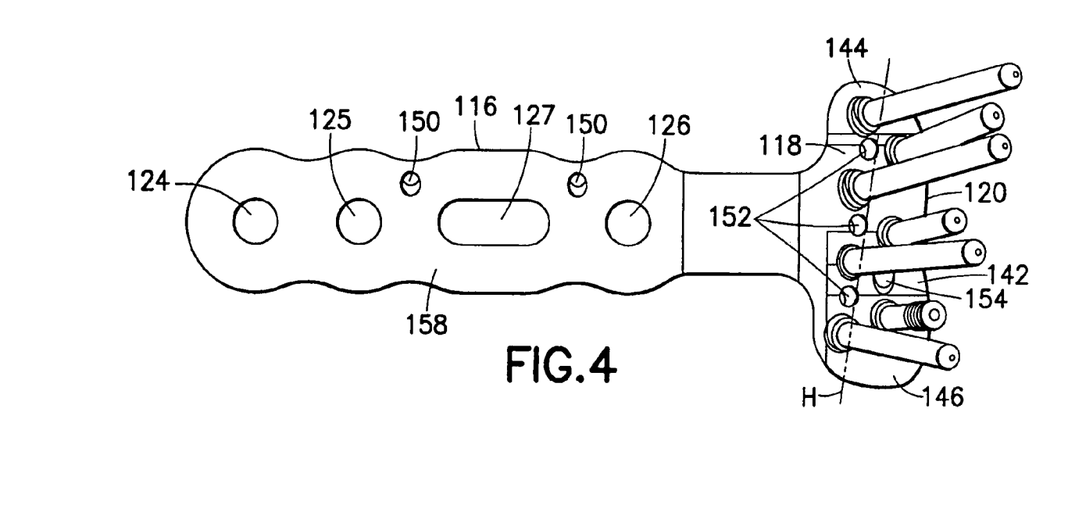
FIG. 4 is bottom view of a right-hand volar plate according to the invention, shown with pegs coupled thereto.

Referring to FIG. 4, the body 116 includes four preferably countersunk screw holes 124, 125, 126, 127 for the extension of bone screws 104 therethrough (FIG. 2). One of the screw holes, 127, is preferably generally oval in shape permitting longitudinal movement of the plate 102 relative to the shaft of a bone screw when the screw is not tightly clamped against the plate. The screw holes may be any hole type for attaching a fixation structure, threaded or non-threaded, for coupling a cortical screw or a locking peg relative to the plate and the underlying bone.

Figure 3:
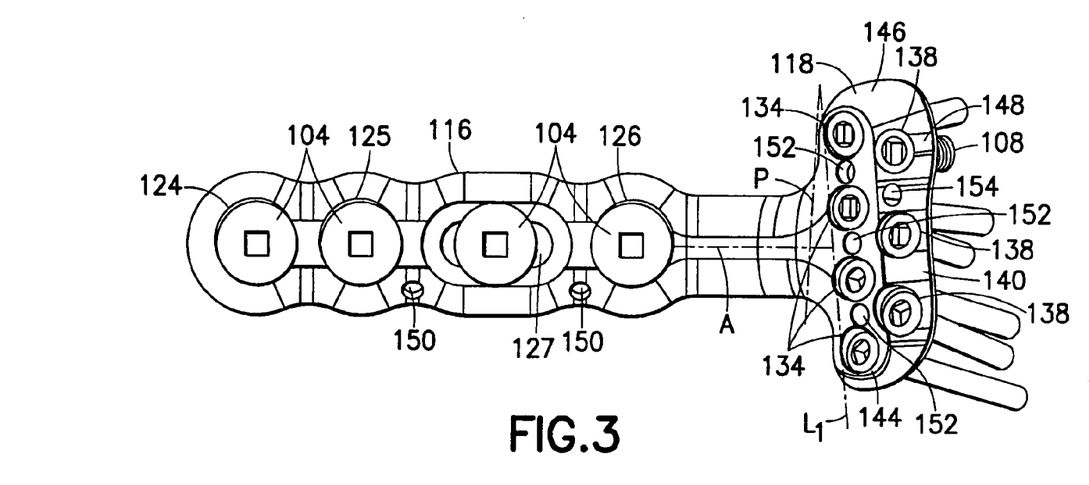
FIG. 3 is top view of a right-hand volar plate according to the invention, shown with pegs and screws.
Figure 14:
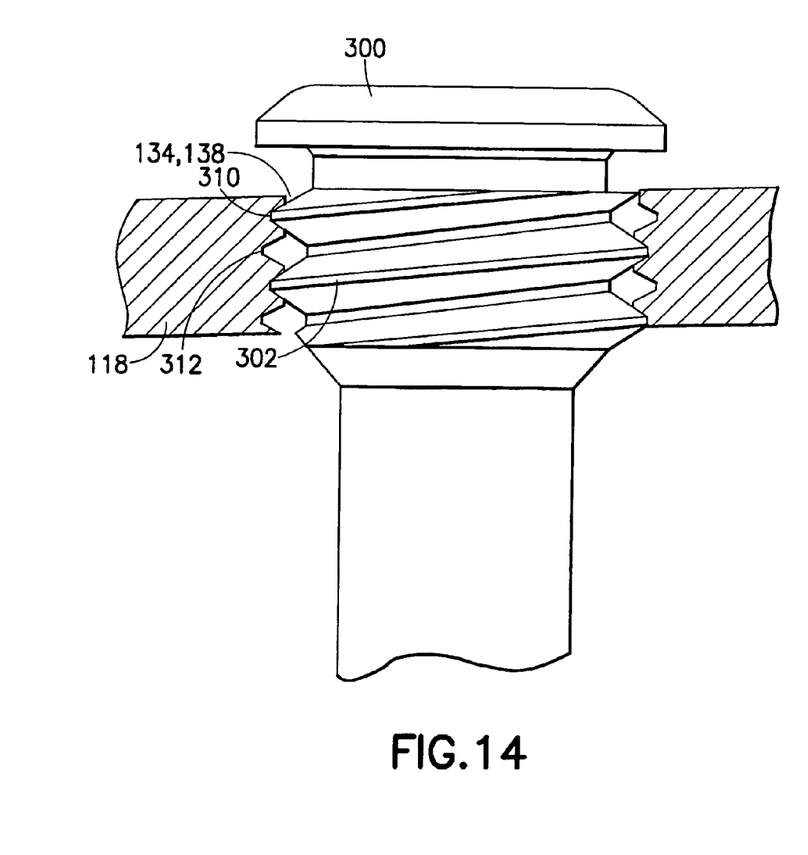
FIG. 14 is a schematic illustration of a peg coupled within a peg hole.

Referring to FIGS. 3 and 4, according to one preferred aspect of the plate 102, the head portion 118 includes a proximal first set of threaded preferably cylindrical peg holes 134 (for placement of pegs 106 and/or 108 therein) and a relatively distal second set of threaded preferably cylindrical peg holes 138 (for placement of pegs 106 and/or 108 therein). Referring to FIG. 14, the peg holes 134, 138 optionally have double lead internal threads 210, 212, with entries to these threads located 180° apart. Each of the threads 210, 212 is adapted to mate securely with the thread 202 on a peg head 200, however thread 202 can only mate with one of the threads 210, 212 at any one time. The depth of each of the double lead internal threads 210, 212 is preferably substantially less than the depth of thread 202 on peg head 200, and most preferably approximately one half such depth. The double lead threads 210, 212 facilitate alignment and entry of the peg head thread 202 into a thread of the peg hole, as the peg will require rotation by at most 180° in a single rotational direction before thread engagement. Furthermore, in distinction from a conical head and hole, the cylindrical double lead thread hole does not compromise the secure interlock attained from full travel of the thread 202 of the peg head 200 through the cylindrical peg hole 134, 138 through, e.g., 900°. Moreover, the combination of double lead thread holes and a single helical thread on the peg head reduces cross-threading by fifty percent.

Referring back to FIGS. 3 and 4, the peg holes 134 of the first set are arranged substantially parallel to a line $L_1$ that is preferably slightly skewed (e.g., by 5°-10°) relative to a perpendicular P to the axis A of the body portion 116. Axes through the first set of peg holes (indicated by the pegs 106 extending therethrough) are preferably oblique relative to each other, and are preferably angled relative to each other in two dimensions, generally as described in commonly-owned U.S. Pat. No. 6,364,882, which is hereby incorporated by reference herein in its entirety. More particularly, the pegs 106 are angled so as to extend through the sub-chondral bone just below and parallel to the curving articular surface of the distal radius so as to provide support for the central and/or dorsal aspects of the subchondral bone. This oblique orientation of the pegs operates to stabilize the central and/or dorsal aspects of the subchondral bone of the articular surface relative to the head 118 of the plate 102 even where such pegs 106 do not have threaded shafts.

The second set of peg holes 138 is provided relatively distal of the first set of peg holes 134 and is most preferably primarily located in the tapered buttress 120. Each of the peg holes 138 preferably defines an axis that is oblique relative to the other of peg holes 136 and 138. Thus, each and every peg 106, 108 when positioned within respective peg holes 134, 138 defines a distinct axis relative to the other pegs. Moreover, the axes of the peg holes 138 are preferably oriented relative to the axes of peg holes 134 such that pegs 106, 108 within peg holes 138 extend (or define axes which extend) between pegs (or axes thereof) within peg holes 134 in an interleaved manner and provide support for volar aspects of the subchondral bone of the distal radius. The oblique orientation of the pegs provides such stabilization even where such pegs 106 do not have threaded shafts.

Referring specifically to FIGS. 1, 2, 5, 6, 15 and 16, according to another preferred aspect of the plate 102, in order to approximate the anatomy for ideal fracture support and maintain a low profile, the upper and lower surfaces 140, 142, respectively of the buttress 120 are contoured relative to provide the least amount of interference with the anatomy. The lower surface 142 is contoured for the anatomical structure of the radius bone 900 that it will overlie. In particular, the lower surface 142 at an ulnar-side portion 144 of the head portion 118 is elevated primarily in a distal direction to accommodate the bulky volar rim 902 of the lunate fossa 904 (such volar rim commonly separating to become a volar marginal fragment in many fractures), and the lower surface at a radial side portion 146 of the head 118 is elevated laterally relative to the remainder of the head to accommodate a prominence 906 at the radial aspect of the radius bone, as indicated by the visibility of these lower surfaces in the side views of FIGS. 1, 2 and 16 and the head-on view of FIG. 6. The contoured shape (with generally three defined planes) provides a stable shape that prevents rocking of the plate on the bone.

In addition, the upper and lower surfaces 140, 142 are contoured to present a reduced profile and therefore limit potential interference with the tendons and soft tissue near the edge of the articular surface. To that end, the buttress 120 is tapered to prevent irritation of tendons and soft tissue extending over a boney ridge (referred to herein as 'the watershed line') and identified by dark line 910 on the volar side of the radius where the slope of the bone changes from ascending (up from the diaphysis 912) to descending (the distal articular portion 904 of the radius). On the proximal (or ascending) portion of the bony ridge there exists a concavity 916 in the radius bone, and the head 118 of the plate 102 is contoured to seat at least partially within the concavity with the tapered buttress 120 terminating below the boney ridge so that the tendons and soft tissues can move over the boney ridge without any interference from the plate. In accord with accommodating the anatomy, the tapered edge 121 of the buttress 120 tapers substantially from the bone contacting surface along the ulnar side of the buttress (with a relatively shallow change in slope from the proximal portion of the head to the distal edge of the buttress) and substantially tapers from the upper surface along the radial side (with a relatively steeper change in slope from the proximal portion of the head to the distal edge of the buttress). The distal edge 121 of the buttress 120 defines an elongate S-shape on a right-hand plate, an elongate Z-shape on a left-hand plate.

A distal extension 148 is also provided at the ulnar side portion 146 of the plate to further buttress the volar rim 902 of the articular socket of the radius bone, thereby providing support to maintain the wrist within the articular socket. This is contrary to prior art plates which, if they provide laterally asymmetrical support, provide such additional support on the radial side due to the apparent radial extension of the radius in view of the styloid process 914. However, the styloid process 914 is on the descending side of the boney ridge 910 (discussed above) and not suitable for buttressing. (According to the present invention, the styloid process 914 is captured by one of the pegs.) The radius bone 900 on the ascending side has an enlarged area at the ulnar side at the volar rim 902 which the distal extension 148 buttresses. In particular, the proximal portion of the head portion 118 (rear of the buttress 120 to the proximal edge of the head portion) is approximately 5.3 mm deep, while the distal edge of the buttress is not straight so that the buttress has a varying proximal-distal depth. From a proximalmost location of the buttress 120 aligned with the radialmost hole of the first set of peg holes 134 the buttress has a proximal-distal depth of 2.28 mm (where the head portion rounds off), from a proximalmost location of the buttress aligned with the adjacent hole of the first set of peg holes the buttress has a proximal-distal depth of approximately 2.8 mm (along a straight portion substantially parallel to line $L_1$), from a proximalmost location of the buttress aligned with the adjacent hole thereof of the first set of peg holes the buttress has a proximal-distal depth of 3.56 mm (along an approach to the ulnar support), and from a proximalmost location of the buttress aligned with the ulnarly located hole of the first set of peg holes the buttress has a proximal-distal depth of 4.57 mm (at the distal extension 148).

Referring specifically to FIGS. 3 and 4, according to a further preferred aspect of the invention, the plate 102 is provided with body alignment holes 150 and proximal head alignment holes 152a, 152b, 152c (generally 152), each sized to 'closely accept' standard Kirschner wires (K-wires), e.g., 1.55 mm in diameter, in at least in dimension. By 'closely accept' it is meant that when a K-wire is inserted into any of the alignment holes, the K-wire is generally in a fixed angle relationship with the alignment hole such that there is preferably less than five degrees (5°) of relative angular movement therebetween, and more preferably less than three degrees (3°) of relative angular movement therebetween. In order to effect such fixed angle relationship, the clearance between the K-wire and the alignment hole is preferably 0.002 inch, and more preferably 0.001 inch.

The plate 102 also includes a distal head alignment hole 154 is provided between the central and radial-side peg holes 138, and preferably has a circular upper opening, and flares to a laterally oblong lower opening, as shown best in FIG. 6. In view thereof, the alignment hole 154 closely accepts a K-wire in a proximal-distal dimension and permits a degree of angular movement relative thereto in a lateral dimension (preferably approximately 30°). Alternatively, the upper opening can be oblong and the lower opening circular. As yet another alternatively, alignment hole 154 can be laterally oblong at upper and lower portions or throughout, but proximally-distally dimensioned to closely receive a K-wire. That is, while a K-wire can be angled within the oblong portion of the hole, the close fitting walls are of sufficient length to hold a K-wire in a fixed angle relationship relative to the walls. The distal head alignment hole 154 has specialized application in the correction of metaphyseal deformities, as described in more detail below.

The upper openings of all the alignment holes 150, 152, 154 are substantially smaller in diameter (e.g., by thirty to fifty percent) than the shafts of screws 104 (approximately 3.15 mm in diameter) and the shafts of pegs 106, 108 (approximately 2.25 mm in diameter).

The body alignment holes 150 are longitudinally displaced along the body portion 116 and provided at an oblique angle (preferably approximately 15°, as shown in FIG. 5) relative to a line normal relative to the lower surface 158 of the body portion 116. Alternatively, the body alignment holes 150 may be oblong in the transverse direction but fixed angle in the longitudinal direction. This enables the surgeon to drill perpendicular to the bone surface.

The proximal head alignment holes 152 alternate with the peg holes 134. A tangent line H to the distalmost points of the head alignment holes 152 is preferably substantially coincident or closely parallel with a line tangent to points on the circumferences of the shafts of pegs 106 inserted through holes 134 adjacent the head portion 118 of the plate 102. With respect to the proximal head alignment holes, it is appreciated that a shaft 106a of a peg is generally smaller in diameter than a head 106b of a peg (FIG. 6). Thus, a line tangent to the peg holes 134 (each sized for receiving the head 106b of peg 106) will be closely located, but parallel, to a line tangent to a distalmost point on the respective alignment hole 152. Nevertheless, for purposes of the claims, both (i) a tangent line which is preferably substantially coincident with a line tangent to points on the circumferences of the shafts of pegs and (ii) a tangent line to a set of peg holes shall be considered to be "substantially coincident" with a line tangent to a distalmost point of an alignment hole 152. Axes through alignment holes 152 preferably generally approximate (within, e.g., 3-5°) the angle of an axis of an adjacent peg hole 134. Moreover, the axis through each proximal alignment hole 152 is preferably oriented substantially equidistantly between the axes through peg holes 134 on either side of the alignment hole. As such, K-wires 110 inserted into the proximal alignment holes 152 (and extending coaxial with the axes therethrough) define a virtual surface which approximately substantially the same virtual surface defined by pegs 106, 108 inserted through peg holes 134. This common virtual surface follows the dorsal aspect of the subchondral bone. Thus, as described in more detail below, the insertion of K-wires 110 through proximal alignment holes 152 in the plate 102 provides a visual cue to the surgeon which anticipates the location of subsequently placed pegs 106, 108.

The plate 102 may be used in at least two different applications: fracture fixation and metaphyseal osteotomies. In either application, an incision is first made over the distal radius, and the pronator quadratus is reflected from its radial insertion exposing the entire distal radius ulnarly to the distal radioulnar joint. For fracture fixation, the surgeon reduces the fracture and aligns the plate 102 thereover. The surgeon then either attaches the plate to the proximal fragment with a screw or drills one or two K-wires 110 through respective body alignment holes 150, and one or more K-wires through selected proximal head alignment holes 152 at the location at which the surgeon believes the pegs 106, 108 should be placed based on anatomical landmarks and/or fluoroscopic guidance. The K-wires temporarily fix the orientation of the plate to the distal fragment. While the fixation is temporary, it is relatively secure in view of the fact that the body alignment holes 150, proximal head alignment holes 152, and K-wires 110 therethrough are angled in different orientations relative to the lower surface of the plate. The K-wires 110 not only fix the plate 102 to the bone, but also prevent angular displacement of bone fragments. Once the alignment is so fixed, the fracture is examined, e.g., under fluoroscopy, to determine whether the K-wires 110 are properly aligned relative to the articular surface. As the axes of the proximal head alignment holes 152 correspond to axes of the adjacent peg holes 134, the fluoroscopically viewed K-wires 110 anticipate whether the pegs 106, 108 will be properly oriented. If the placement is correct, the K-wires 110 maintain the position of the plate 102 over the fracture while holes in the bone are drilled through the screw holes 124, 125, 126, 127 for the screws 104 and peg holes 134, 138 for pegs 106, 108, with confidence that the locations and orientation of the screws and pegs inserted therein are anatomically appropriate. In addition, where pegs 108 are used, due to the difference in pitch between the head threads 202 and shaft threads 206, slight compression of a distally or dorsally displaced fragment toward a proximal fragment or bone (e.g., 1.5 mm of travel) is effected even though the head 200 will lock relative to the head 118 of the plate 100. Once the screws 104 and pegs 106, 108 have secured the plate to the bone, the K-wires are preferably removed.

If fluoroscopic examination indicates that placement of the K-wires 110 is not optimal, the K-wires can be removed and the surgeon has an opportunity to relocate and/or reorient the K-wires and drill again. Since each K-wire is of relatively small diameter, the bone is not significantly damaged by the drilling process and the surgeon is not committed to the initial drill location and/or orientation.

The pegs 106 within the pegs holes 134 define projections that provide support at the central and/or dorsal aspects of the subchondral bone. The pegs 106 within peg holes 138 define projections that provide support at the volar aspect behind the articular surface of the bone surface. The sets of pegs 106, 108 through peg holes 134, 138 laterally overlap so that the pegs preferably laterally alternate to provide closely-spaced tangential cradling of the subchondral bone. A preferred degree of subchondral support is provided with four peg holes 134 (and associated pegs) through the proximal portion of the head 118 of the plate, and three peg holes 138 (and associated pegs) through the distal portion of the head 118. The fracture fixation system thereby defines a framework which substantially tangentially supports the bone fragments in their proper orientation. In accord with an alternate less preferred embodiment, suitable support may also be provided-where the pegs 106 and 108 are parallel to each other or in another relative orientation or with fewer peg holes and/or pegs.

The method particularly facilitates stabilization of a metaphyseal fracture which may include a smaller distal bone fragment spaced apart from a larger proximal fragment. The insertion of one or more threaded pegs 108 (preferably in conjunction with several non-threaded pegs 106) in which the threads on the shaft 206 have a pitch greater than the threads 202 on the head 200 causes a limited amount of compression of the smaller distal bone fragment toward the larger proximal bone fragment, and thus toward the plate.

Figure 7:
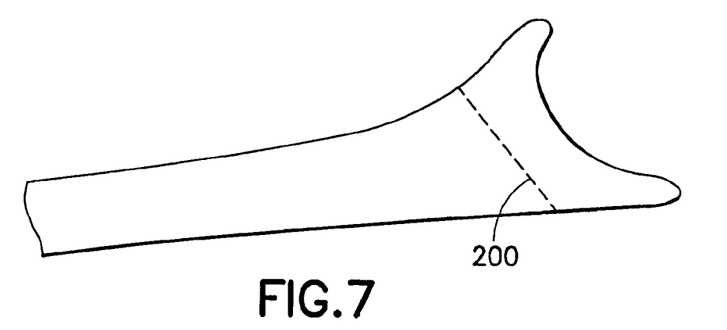
FIGS. 7 through 12 illustrate a method of performing an osteotomy of the distal radius according to the invention.
Figure 8:
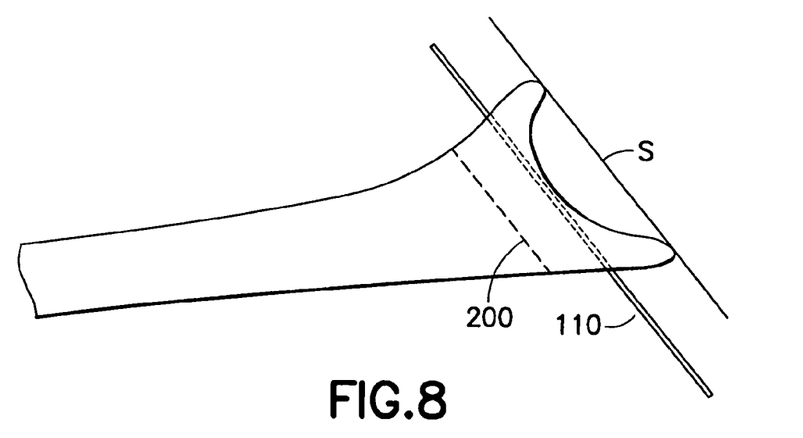
Figure 9:
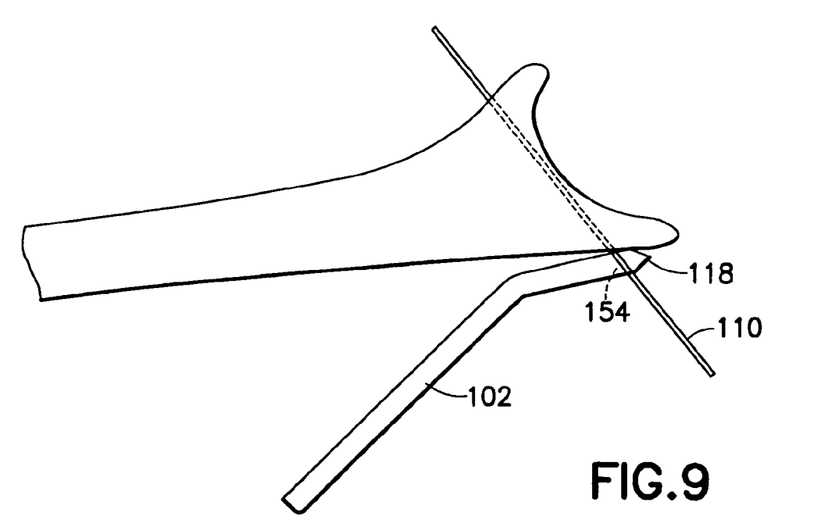
Figure 10:
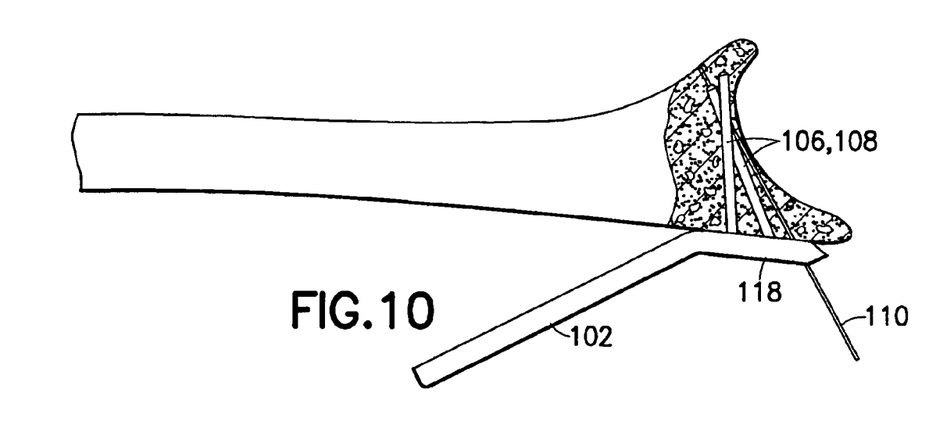
Figure 11:
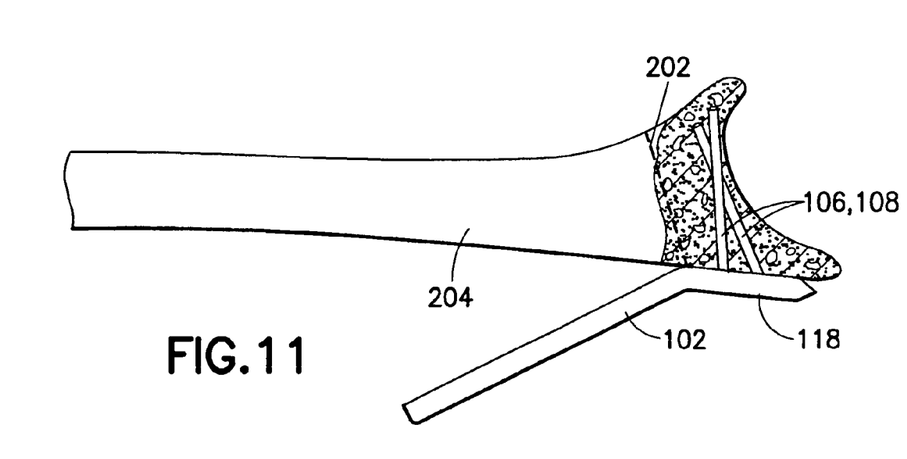
Figure 12:
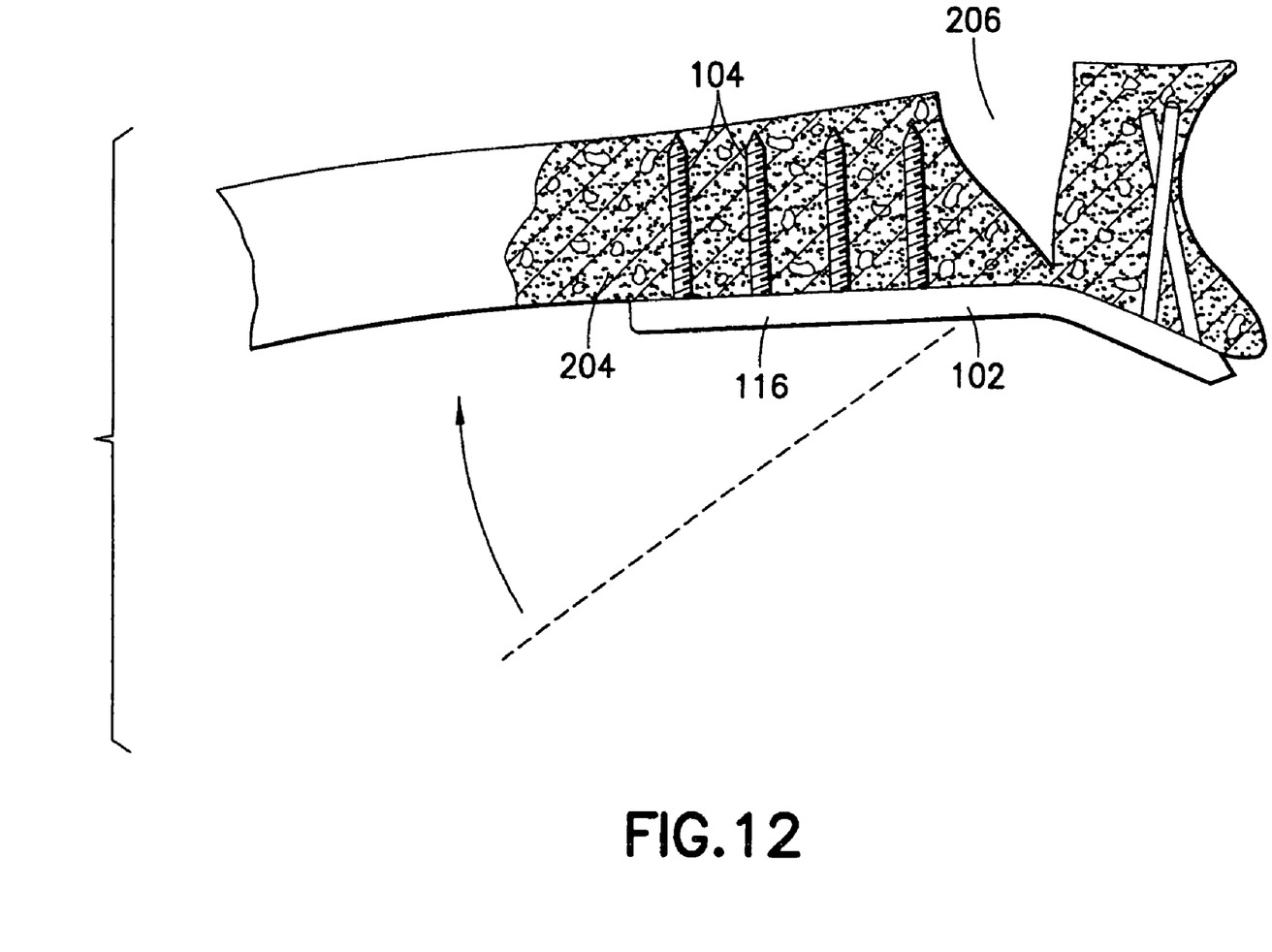

According to a second use, the plate may be used in an osteotomy to correct a metaphyseal deformity 200 (such as malformed fracture or congenital deformity), as shown in FIG. 7. For such purposes, a K-wire 110 is drilled into the bone parallel to the articular surface S in the lateral view under fluoroscopy (FIG. 8). The free end of the K-wire 110 is guided through the oblong distal head alignment hole 154, and the plate 102 is slid down over the K-wire into position against the bone (FIG. 9). The oblong alignment hole 154 permits the plate 102 to tilt laterally over the K-wire 110 to sit flat on the bone, but does not permit tilting of plate relative to the K-wire in the anterior-posterior (sagital) plane. This is important, as visualization to align the K-wire parallel relative to the articular surface will not disclose whether the K-wire is angled in the lateral direction. Thus, the plate is brought over the K-wire in the correct anterior-posterior alignment, but may then be laterally tilted on the K-wire to effect proper medial-lateral placement of the plate on bone. Once the plate 102 is seated against the bone, the surgeon drills holes in the bone in alignment with the peg holes 134, 138 (FIG. 3) and then fixes the plate relative the bone with pegs 106, 108 (FIG. 10). The K-wire 110 is removed. The bone is then saw cut at 202 proximal the location of the head 118 of the plate 102 (FIG. 11), and the body 116 of the plate is levered toward the proximal diaphyseal bone 204, creating an open wedge 206 at the deformity (FIG. 12). When the body 116 of the plate 102 is in contact and longitudinal alignment with the diaphysis of the bone, the bone distal of the cut has been repositioned into the anatomically correct orientation relative to the shaft of the bone. The body 116 of the plate 102 is then secured to the bone with screws 104. Post-operatively, the open wedge in the bone heals resulting in an anatomically correct distal radius.

While fixed single-angle pegs have been disclosed for use with the plate (i.e., the pegs may be fixed in respective threaded peg holes 134, 136 only coaxial with an axis defined by the respective peg holes), it is appreciated that an articulating peg system, such as that disclosed in co-owned U.S. Pat. No. 6,440,135 or co-owned and co-pending U.S. Ser. No. 10/159,612, both of which are hereby incorporated by reference herein in their entireties, may also be used. In such articulating peg systems, the peg holes and pegs are structurally adapted such that individual pegs may be fixed at any angle within a range of angles. In addition, while less preferable, one or both sets of the pegs may be replaced by preferably blunt tines which are integrated into the plate such that the plate and tines are unitary in construct. Similarly, other elongate projections may be coupled to the plate to define the desired support.

There have been described and illustrated herein embodiments of a fixation plate, and particularly plates for fixation of distal radius fractures, as well as a method of aligning and stabilizing a distal radius fracture and performing an osteotomy. While particular embodiments of the invention have been described, it is not intended that the invention be limited thereto, as it is intended that the invention be as broad in scope as the art will allow and that the specification be read likewise. Thus, while particular preferred materials, dimensions, and relative angles for particular elements of the system have been disclosed, it will be appreciated that other materials, dimensions, and relative angles may be used as well. Further, plates having shapes other than a 'T' may also be used, such as lateral and medial columns (generally 'L'-shaped), and plates having a flared head, provided such plates are dimensioned and configured for placement at the distal radius. In addition, while a particular number of screw holes in the volar plate and bone screws have been described, it will be understood another number of screw holes and screws may be used. Further, fewer screws than the number of screw holes may be used to secure to the plate to the bone. Also, fewer or more peg holes and bone pegs may be used, preferably such that at least two pegs angled in two dimensions relative to each other are provided. In addition, while a particular preferred angle between the head and body has been disclosed, other angles can also be used. Moreover, while the cylindrical double lead thread hole and single thread head interface has been disclosed with respect to a fracture plate for distal radius fractures, it is appreciated that such a system has advantage to other orthopedic stabilization devices such as fragment plates (which may be rectangular in shape or a different shape) and plates specifically designed for fractures of other bones. Similarly, a threaded peg (i.e., locking screw) with threads of different pitches on the head and along the shaft may also be used in other applications. Furthermore, while a double lead thread is preferred for use with a peg having a single thread on its head, it is appreciated that, e.g., a triple lead thread can be used where the entry leads are. angularly offset by 120°. Such will reduce cross threading by two-thirds, but will also reduce hole thread depth further. It will therefore be appreciated by those skilled in the art that yet other modifications could be made to the provided invention without deviating from its spirit and scope.

What is claimed is:

1. A fixation plate for use with a plurality of fixation pegs each having a threaded head, said fixation plate comprising:
a substantially rigid plate having a body portion and a head portion elevated in a Z-direction relative to said body portion, said plate sized to accommodate the anatomy of the volar side of the distal radius bone, said head portion having, a top surface, a lower surface an ulnar side, a radial side, and a buttress portion distally tapering in thickness to a non-linear distal edge, said buttress portion extending greater distally on said ulnar side of said head portion than on said radial side of said head portion,
wherein said plate defines a first set of substantially linearly arranged fixed angle holes proximal said buttress portion and a second set of substantially linearly arranged fixed angle holes at least partially defined in said buttress portion, said first set of holes each defining only one fixed central axis, and at least two of said central axes diverging from each other in a direction from said top surface to said lower surface of said head portion, and at least two of said central axes being oblique in two dimensions relative to each other.

2. A fixation plate according to claim 1, wherein:
each of said first set of fixed angle holes is structurally adapted to engage the threaded head of one of the fixation pegs and retain the fixation peg in a fixed angle relationship with said plate.

3. A fixation plate according to claim 2, wherein:
each of said first set of fixed angle holes is threaded.

4. A fixation plate according to claim 3, wherein:
each of said first set of fixed angle holes defines an axis which is obliquely oriented in at least one dimension relative to the other respective axes of said first set of fixed angle holes.

5. A fixation plate according to claim 4, wherein:
each of said first set of fixed angle holes defines an axis which is obliquely oriented in two dimensions relative to the other axes of said first set of fixed angle holes.

6. A fixation plate according to claim 1, wherein:
said first set of fixed angle holes includes at least four fixed angle holes.

7. A fixation plate according to claim 6, wherein:
said second set of fixed angle holes includes at least two fixed angle holes.

8. A fixation plate according to claim 7, wherein:
said second set of fixed angle holes includes at least three fixed angle holes.

9. A fixation plate according to claim 7, wherein:
each of said second set of fixed angle holes is structurally adapted to engage the threaded head of one of the fixation pegs and retain the fixation peg in a fixed angle relationship with said plate.

10. A fixation plate according to claim 9, wherein:
each of said second set of fixed angle holes is threaded.

11. A fixation plate according to claim 10, wherein:
each of said second set of fixed angle holes defines an axis which is obliquely oriented in at least one dimension relative to the other axes of said second set of fixed angle holes.

12. A fixation plate according to claim 11, wherein:
each of said second set of fixed angle holes defines an axis which is obliquely oriented in two dimensions relative to the other axes of said second set of fixed angle holes.

13. A fixation plate for distal radius fractures use with a plurality of fixation pegs each having a threaded head, said fixation plate comprising:
a substantially rigid plate having a body portion and a head portion elevated in a Z-direction relative to said body portion, said head portion including a lower surface, a central portion, a radial side and an ulnar side, said plate sized to accommodate the anatomy of the volar side of the distal radius bone,
said plate defining a first set of substantially linearly arranged holes extending in a generally medial-lateral direction, and a buttress portion distal of said first set of holes,
said buttress portion extending greater distally on said ulnar side than on said radial side to support the volar lip of the lunate fossa, and
wherein said lower surface at said ulnar side is elevated in the Z-direction relative to said lower surface at said central portion and said lower surface at said radial side is elevated in the Z-direction relative to said lower surface at said central portion.

14. A fixation plate according to claim 13, wherein:
said buttress at least partially includes a second set of substantially linearly arranged holes, substantially parallel in arrangement to said first set.

15. A fracture fixation plate for distal radius fractures, comprising:
a substantially rigid plate having a body portion and a head portion elevated in a Z-direction relative to said body portion, said plate sized to accommodate the anatomy of the volar side of the distal radius bone, said head portion defining a first set of holes,
wherein said head portion includes a bone contacting surface having an ulnar portion which is further elevated in the Z-direction as said ulnar portion extend distally, and a radial side portion which is further elevated in the Z-direction as said radial side portion extends laterally, each being elevated relative to a remainder of said bone contacting surface of said head portion between said ulnar and radial side portions.

16. A fracture fixation plate according to claim 15, wherein:
said first set of holes are structurally adapted to engage and retain a plurality of elements each at a fixed angle relative to said head portion.

17. A fracture fixation plate according to claim 16, wherein:
said first set of holes are threaded.
18. A fracture fixation plate according to claim 15, wherein:
said first set of holes are substantially linearly arranged.
19. A fracture fixation plate according to claim 18, wherein:
said first set of holes are substantially arranged in a medial-lateral direction.

20. A fracture fixation plate according to claim 15, wherein:
said head portion tapers toward a distal edge.
21. A fracture fixation plate according to claim 13, wherein:
said buttress portion tapers in thickness in a distal direction.

* * * * *